US012669434B2

(12) United States Patent
Yan et al.

(10) Patent No.: US 12,669,434 B2
(45) Date of Patent: Jun. 30, 2026

(54) OPTICAL SYSTEM FOR TRIGLYCERIDE INSPECTION

(71) Applicant: Taiwan RedEye Biomedical Inc., Hsinchu City (TW)

(72) Inventors: Shuo-Ting Yan, Hsinchu City (TW); I-Hua Wang, Hsinchu City (TW); Chen-Chung Chang, Hsinchu City (TW)

(73) Assignee: Taiwan RedEye Biomedical Inc., Hsinchu City (TW)

( * ) Notice: Subject to any disclaimer, the term of this patent is extended or adjusted under 35 U.S.C. 154(b) by 719 days.

(21) Appl. No.: 17/940,068

(22) Filed: Sep. 8, 2022

(65) Prior Publication Data

US 2024/0085322 A1     Mar. 14, 2024

(51) Int. Cl.
| | |
|---|---|
| *G01N 21/53* | (2006.01) |
| *A61B 5/00* | (2006.01) |
| *A61B 5/145* | (2006.01) |
| *A61B 5/1455* | (2006.01) |
| *A61B 5/1495* | (2006.01) |
| *E03D 11/00* | (2006.01) |
| *G01N 21/359* | (2014.01) |
| *G01N 21/47* | (2006.01) |

(52) U.S. Cl.
CPC ........... *G01N 21/53* (2013.01); *A61B 5/0004* (2013.01); *A61B 5/14546* (2013.01); *A61B 5/1455* (2013.01); *A61B 5/1495* (2013.01); *A61B 5/6891* (2013.01); *E03D 11/00* (2013.01); *A61B 2562/0238* (2013.01); *G01N 2201/12746* (2013.01)

(58) Field of Classification Search
CPC ......... G01N 21/53; G01N 2201/12746; G01N 21/359; G01N 21/4738; A61B 5/0004; A61B 5/14546; A61B 5/1455; A61B 5/1495; A61B 5/6891; A61B 2562/0238; A61B 5/0075; E03D 11/00
USPC ........................................................ 600/322
See application file for complete search history.

(56) References Cited

U.S. PATENT DOCUMENTS

| | | | | |
|---|---|---|---|---|
| 2016/0313176 A1* | 10/2016 | Lee | ..................... | A61B 5/02416 |
| 2018/0092602 A1* | 4/2018 | Hall | ..................... | A61B 5/1102 |
| 2018/0137609 A1* | 5/2018 | Barker | ..................... | G06T 5/92 |
| 2018/0214088 A1* | 8/2018 | Newberry | ............. | A61B 5/6817 |
| 2022/0240816 A1* | 8/2022 | Shimizu | ................. | G06F 17/11 |

* cited by examiner

*Primary Examiner* — Devin B Henson
*Assistant Examiner* — Molly Halprin
(74) *Attorney, Agent, or Firm* — Anova Law Group, PLLC

(57) ABSTRACT

An optical system for triglyceride inspection is disclosed. The optical system includes a first light source, a second light source, an optical sensor, and an electronic device, wherein the electronic device is configured to: control the first light source to emit white light onto a skin of a subject, causing a first scattered light to be produced from the skin; control the second light source to emit detection light onto the skin, causing a second scattered light to be produced from the skin; collect the first and second scattered lights; calculate an estimated reflectance, a calibration coefficient, and an estimated internal turbidity based on the first and second scattered lights; and employ the calibration coefficient to calibrate the estimated internal turbidity so as to obtain a measured internal turbidity. Simply put, the optical system can correct optical measurement errors caused by variations in skin tone.

9 Claims, 6 Drawing Sheets

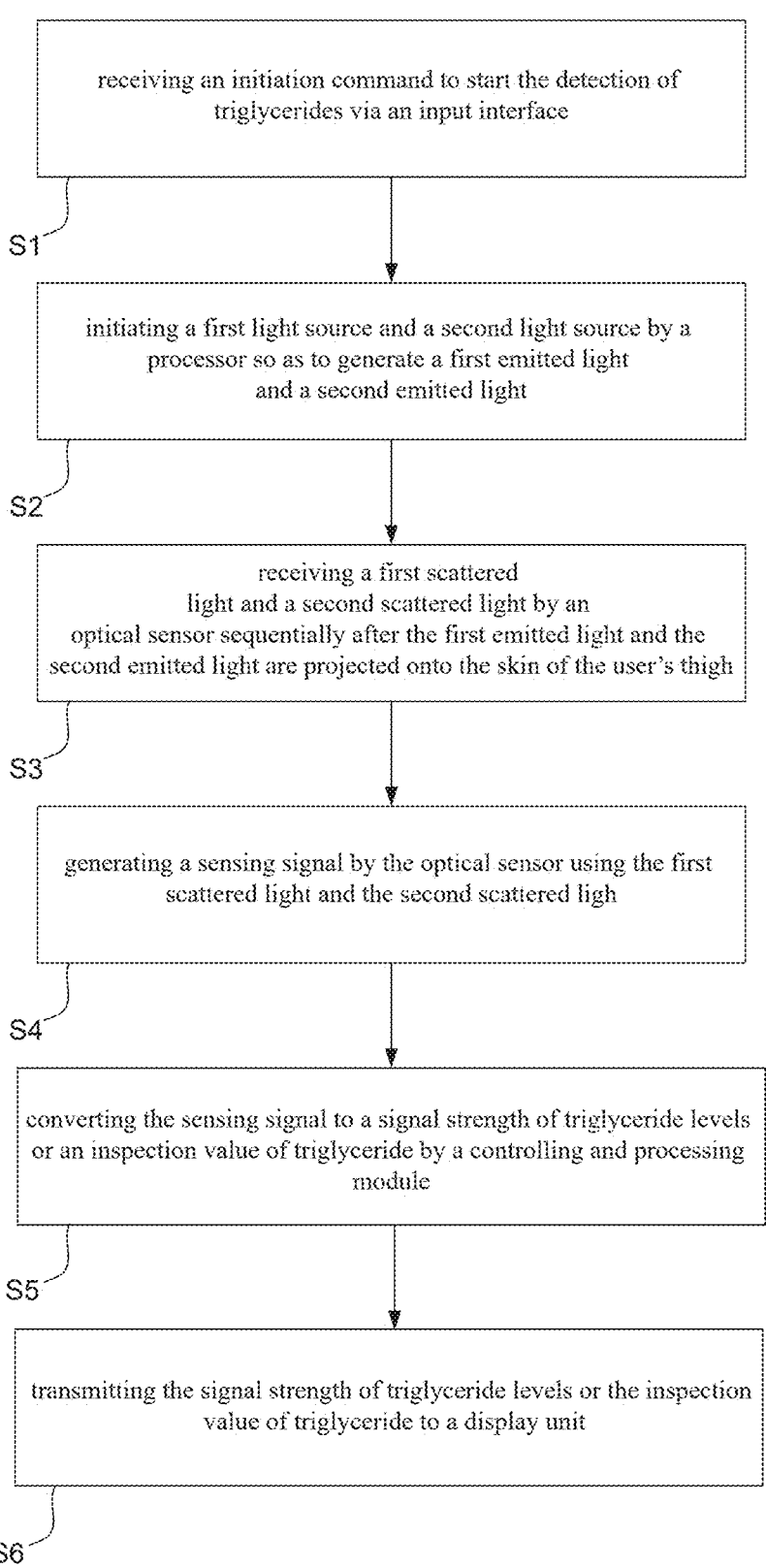

receiving an initiation command to start the detection of triglycerides via an input interface

S1 initiating a first light source and a second light source by a processor so as to generate a first emitted light and a second emitted light

S2 receiving a first scattered light and a second scattered light by an optical sensor sequentially after the first emitted light and the second emitted light are projected onto the skin of the user's thigh

S3 generating a sensing signal by the optical sensor using the first scattered light and the second scattered ligh

S4 converting the sensing signal to a signal strength of triglyceride levels or an inspection value of triglyceride by a controlling and processing module

S5 transmitting the signal strength of triglyceride levels or the inspection value of triglyceride to a display unit

OPTICAL SYSTEM FOR TRIGLYCERIDE INSPECTION

BACKGROUND OF THE INVENTION

1. Field of the Invention

The present invention relates to the technical field of the optical system for triglyceride inspection, and more particularly to an optical system for triglyceride inspection installed on a toilet seat and a toilet containing the system.

2. Description of the Prior Art

Triglycerides (TGs, often referred to as neutral fats) are a type of blood fat in the human body. When a person eats, the body converts any calories it does not need to use immediately into triglycerides. The triglycerides are stored in fat cells of the human body. Later, hormones release triglycerides for energy between meals. If the person regularly eats more calories than he burns, particularly from high-carbohydrate foods, then he may have high triglycerides, i.e. hypertriglyceridemia, resulting in visceral fat and subcutaneous fat and leading to obesity, fatty liver, cardiovascular disease, etc. High levels of triglycerides in the blood are usually a high-risk factor for atherosclerosis, cardiovascular disease, and stroke, so triglyceride levels can be used as one of the biochemical indicators to assess the risk of cardiovascular disease.

In general, the normal levels of triglycerides in adults are less than 150 mg/dl, the borderline high levels are 150 to 199 mg/dL, the high-risk levels are 200 to 499 mg/dL, and the very high-risk levels are greater than 500 mg/dL. Usually, the levels of triglycerides can only be obtained by a blood test. For the conventional technique of blood test, an invasive blood sampling is required to perform on the subject after a subject fast for 8 to 10 hours and must be carried out by a professional medical institution for biochemical analysis to obtain the levels of triglycerides. Therefore, the triglyceride test by blood sampling lacks immediacy and cannot monitor the triglyceride levels in the human body in real-time to achieve home health monitoring and to prevent and reduce the incidence of diseases.

Although the current blood sampling for triglycerides test is usually performed when the subject is fasting (on an empty stomach), triglyceride levels usually increase significantly after eating and drinking, and in the case of cardiovascular disease or stroke occurrence, the patient is not always on an empty stomach. Therefore, it is of some medical significance to perform triglyceride tests immediately, randomly, or without restriction to fasting to help prevent and reduce the occurrence of cardiovascular disease From the above description, the conventional method of blood sampling for triglyceride test is limited by the location and method for implementing the test and cannot monitor the levels of triglycerides in the human body in real-time, so there is still room for improvement. In view of this, inventors of the present application have made great efforts in research and eventually provide the optical system for triglyceride inspection according to the present application.

SUMMARY OF THE INVENTION

The prime objective of the present invention is to disclose an optical system for triglyceride inspection, which can be partially integrated into a toilet seat, or integrated into a toilet. When a user sits on the toilet seat, a light source generates an emitted light that is projected onto the local skin of the thigh of the user. The emitted light will penetrate part of the skin depth, and a scattered light generated therein will be received by an optical sensor. Then the scattered light received by the optical sensor will be used to analyze the signal strength (levels) of triglycerides. In particular, the skin surface characteristics of different users, such as skin tone, skin roughness, number of hairs, etc. may cause the variation in the degree of absorption of the emitted light and the variation in the degree of direct scattering and may subsequently result in a detection error. In response to the skin surface characteristics of different users, the present invention also performs an adaptive compensation for the skin surface characteristics to improve and enhance the accuracy of triglyceride optical detection. In addition, the optical system for triglyceride inspection according to the present invention is a home health monitoring device that can automatically detect the triglyceride levels of the user in real-time without invasive blood sampling. The optical system for triglyceride inspection according to the present invention can help the user to monitor his or her health condition and then proactively prompt the user to adjust the diet immediately to slow down the increase of triglyceride content in the blood and prevent the occurrence of cardiovascular diseases.

For achieving the prime objective mentioned above, the present invention provides an embodiment of an optical system for triglyceride inspection, which can be partially integrated into a toilet seat and comprises:

a plurality of optical sensor modules arranged in the toilet seat, wherein each said optical sensor module comprises:
   a first light source that generates a first emitted light, wherein the first emitted light generates a first scattered light on the skin surface of a user;
   a second light source that generates a second emitted light, wherein the second emitted light partially penetrates the skin of the user and generates a second scattered light; and
   an optical sensor for receiving the first scattered light and the second scattered light and generating a sensing signal using the first scattered light and the second scattered light; and
a controlling and processing module coupled to said plurality of optical sensor modules and comprising a microprocessor and a communication unit;

wherein the microprocessor is configured to control the first light source to generate the first emitted light and the second light source to generate the second emitted light and is configured to receive the sensing signal generated by the optical sensor and to convert the sensing signal into an inspection value of triglyceride, and finally said inspection value of triglyceride is transmitted to a display unit via the communication unit.

In one embodiment, the first light source is a white light source and the second light source is a near-infrared light source.

In one embodiment, the sensing signal is an adaptive calibration function.

In one embodiment, the adaptive calibration function is described in the following steps:
   Step 1: check counts of the reflectance of the first scattered light generated by the white light source, wherein said counts of the reflectance are counted by the optical sensor in the optical system for triglyceride inspection;
   Step 2: obtain a constant C as follows:
   $C = (\text{Counts\_white light})/(\text{Counts\_baseline})$

3

Counts baseline means the definition of a general skin condition;

Step 3: check counts of the reflectance of the second scattered light generated by the near-infrared light source, wherein said counts of the reflectance are counted by the optical sensor in the optical system for triglyceride inspection; Step 4: calculate the internal turbidity Y from step 3, wherein Y is the internal turbidity caused by the triglycerides; and Step 5: show the result Y'=Y/C If C>1, then the skin tone is white or bright; therefore, Y'<Y;

If C<1, then the skin tone is dark, or the skin is rough or hairy; therefore, Y'>Y.

In one embodiment, the wavelength of the near-infrared light source is between 700 and 2500 nm and preferably between 700 and 1100 nm.

In one embodiment, the controlling and processing module is coupled to said plurality of optical sensor modules by wired transmission. In another embodiment, the controlling and processing module may also be coupled to said plurality of optical sensor modules by wireless transmission.

In one embodiment, the communication unit is an Ethernet interface and communicates with the display unit via a local area network and/or the Internet to transmit said inspection value of triglyceride to the display unit.

In one embodiment, the communication unit is a first wireless signal transmission interface and communicates with a second wireless signal transmission interface of the display unit.

In one embodiment, the display unit is a smart toilet control panel, a smartphone, a tablet computer, a smartwatch, a smart bracelet, a door phone, a desktop computer, a laptop computer, an all-in-one computer, or a server computer. The inspection value of triglyceride displayed on the above-mentioned electronic or computer devices can be further uploaded to a cloud server for storage and analysis by health care organizations to provide users with appropriate health care advice or take necessary medical measures to prevent or reduce the occurrence of cardiovascular disease.

In another embodiment, the present invention further provides a toilet comprising an optical system for triglyceride inspection as described above.

BRIEF DESCRIPTION OF THE DRAWINGS

The invention, as well as a preferred mode of use and advantages thereof, will be best understood by referring to the following detailed description of an illustrative embodiment in conjunction with the accompanying drawings, wherein:

FIG. 5 is a flow chart of the optical method for triglyceride inspection according to the present invention; and

4

Figure 6:
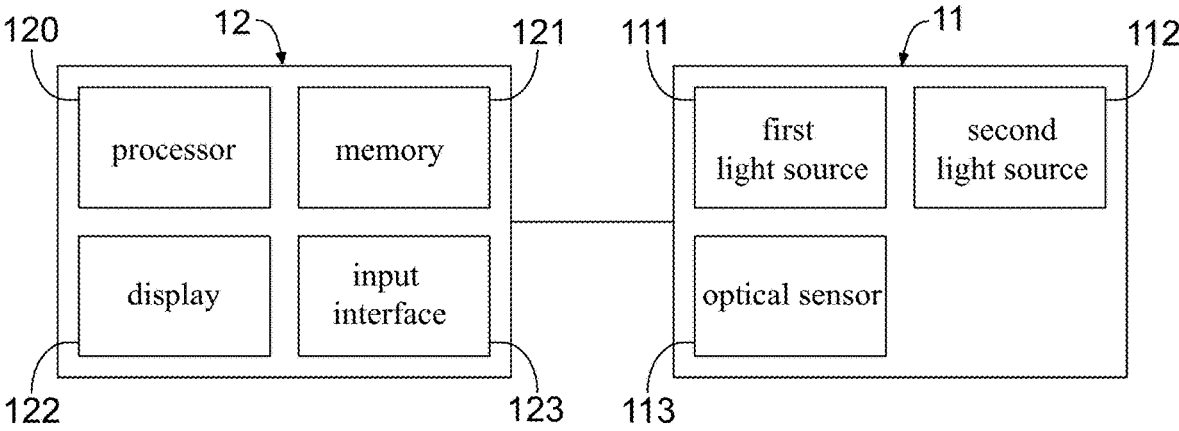

FIG. 6 is a block diagram of the optical system for triglyceride inspection according to the present invention.

DETAILED DESCRIPTION OF THE PREFERRED EMBODIMENTS

To better illustrate the advantages of the optical system for triglyceride inspection according to the present invention and its contributions to the art, preferred embodiments of the present invention will be described in detail concerning the attached drawings hereafter.

First Embodiment

Figure 1:
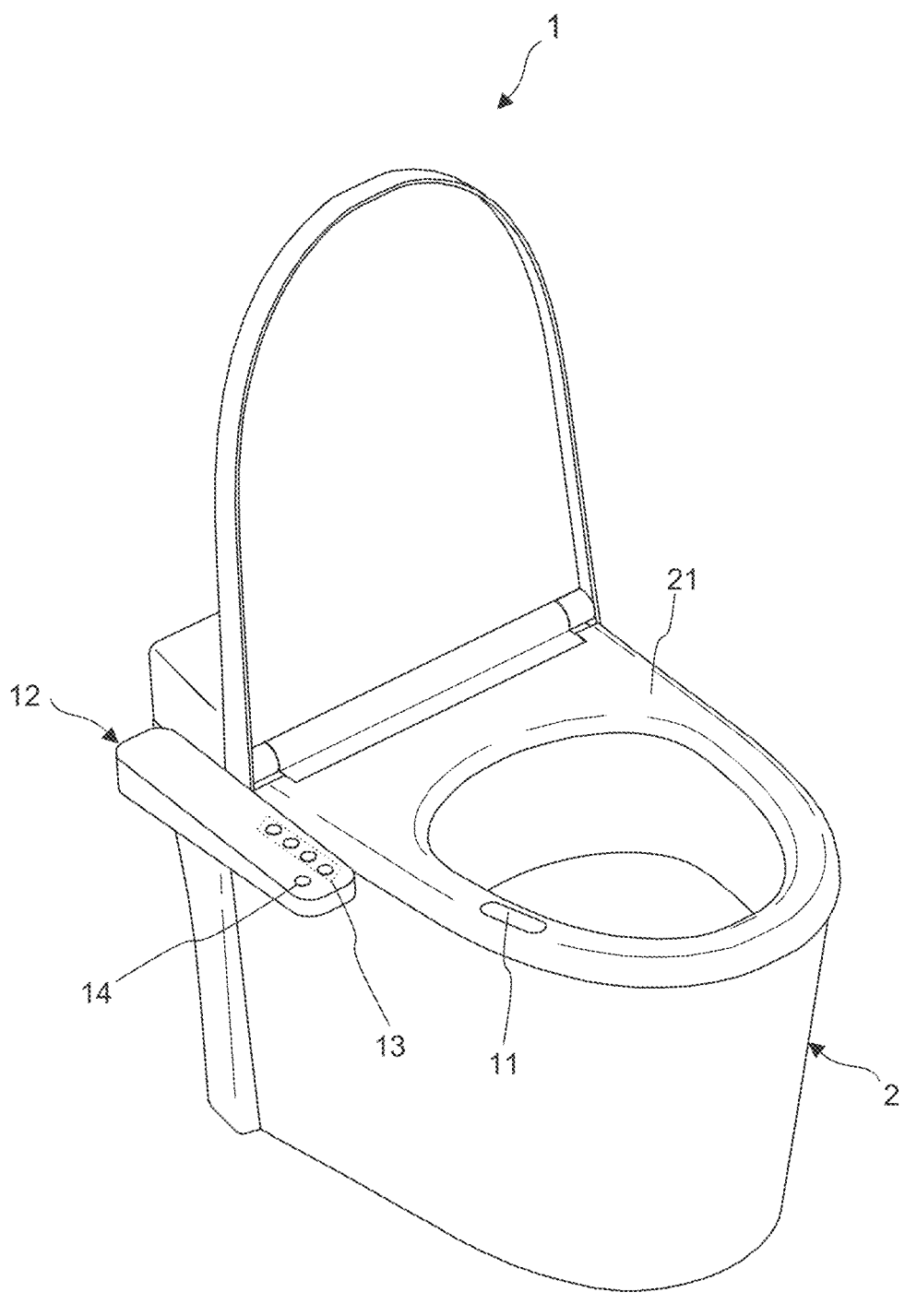
FIG. 1 is a perspective view of a toilet containing the optical system for triglyceride inspection according to the present invention.
Figure 2:
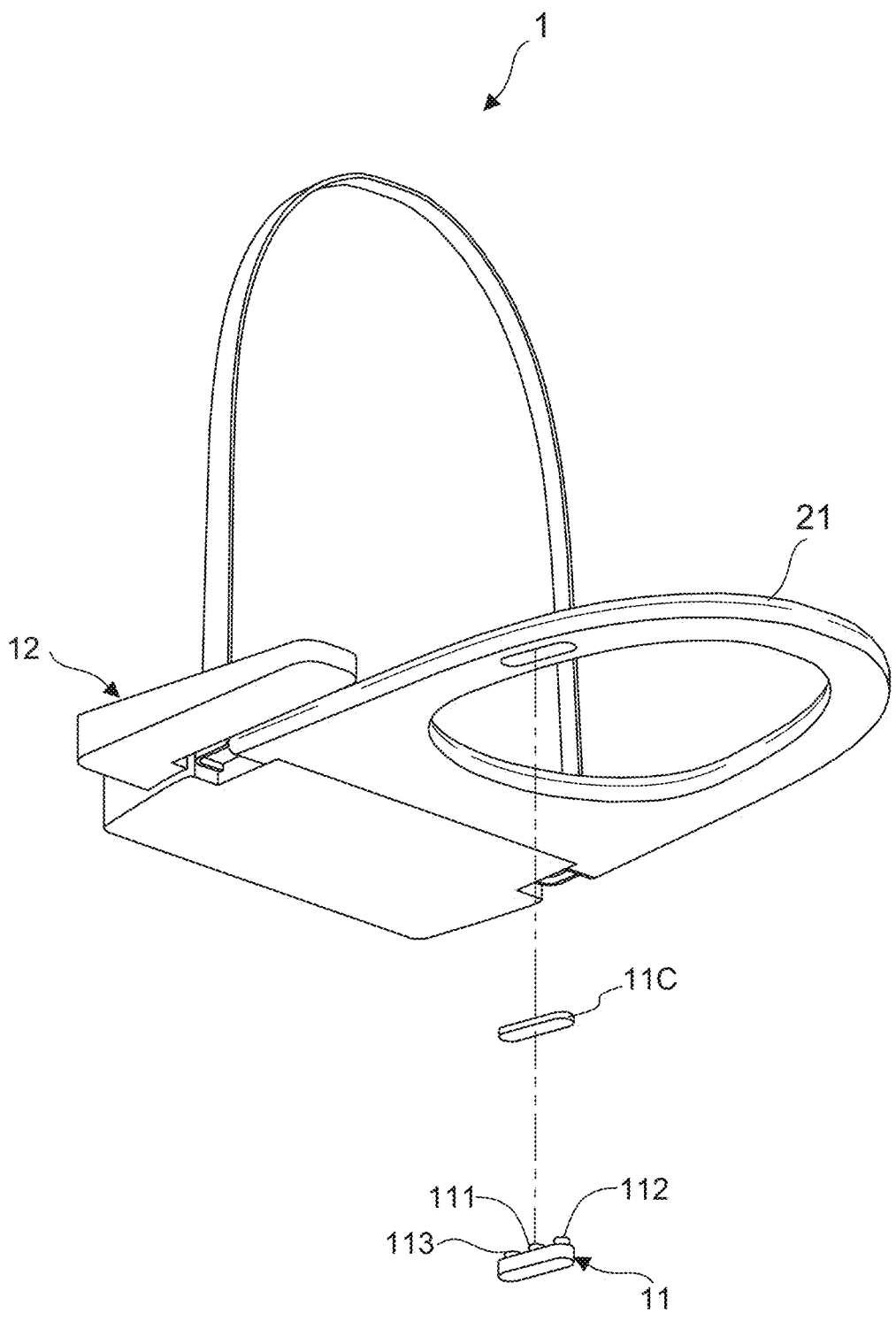
FIG. 2 is an exploded view of the optical sensor module and the toilet seat of the optical system for triglyceride inspection according to the present invention.

FIG. 1 shows a perspective view of a toilet 2 integrated with the optical system 1 for triglyceride inspection according to the present invention, and FIG. 2 shows an exploded view of an optical assembly 11 and a toilet seat 21 of the optical system 1 for triglyceride inspection according to the present invention. As shown in FIG. 1 and FIG. 2, the optical system 1 for triglyceride inspection according to the present invention is partially integrated into a toilet seat 21 and comprises: a optical sensor assembly 11 and an electronicdevice12 coupled to the optical sensor assembly 11, wherein the optical sensor assembly 11 is disposed in the toilet seat 21. As shown in FIG. 6, the electronic device 12 comprises a processor 120, a memory 121, a display 122, and an input interface 123. Further referring to FIG. 3, the optical sensor assembly 11 comprises: a first light source 111, a second light source 112, and an optical sensor 113, wherein the first light source 111 generates a first emitted light 111E and the first emitted light 111E produces a first scattered light 111S on the skin surface of a user, wherein the second light source 112 generates a second emitted light 112E, and the second emitted light 112E partially penetrates the skin of the user and produces a second scattered light 112S. In addition, the optical sensor 113 is configured to receive the first scattered light 111S and the second scattered light 112S and to generate a sensing signal using the first scattered light 111S and the second scattered light 112S. Further, the memory 121 is configured to store instructions, and the processor 120 is configured to execute the instructions so as to control the first light source 111 to generate the first emitted light 111E, to control the second light source 112 to generate the second emitted light 112E, to receive the sensing signal generated by the optical sensor 113, and to convert the sensing signal into an inspection value of triglyceride. Finally, the inspection value of triglyceride is transmitted to the display 122 for presentation to the user.

In a feasible embodiment according to the optical system 1 for triglyceride inspection, the first light source 111 is a white light source and the second light source 112 is a near-infrared light source. In addition, the wavelength of the near-infrared light source is between 700 and 1100 nm.

Furthermore, in the above embodiment, the sensing signal is an adaptive calibration function, and the adaptive calibration function is described in the following steps:

Step 1: check counts of the reflectance of the first scattered light 111S generated by the white light source, wherein said counts of the reflectance are counted by the optical sensor 113 in the optical system 1 for triglyceride inspection;

Step 2: obtain a constant C as follows:

C=(Counts_white light)/(Counts_baseline)

Counts baseline means the definition of a general skin condition;

wherein the Counts baseline is assumed to be 2670, and if the detection value of Counts_white is 2800, then C=2800/2670=1.05;

Step 3: check counts of the reflectance of the second scattered light 112S generated by the near-infrared light source, wherein said counts of the reflectance are counted by the optical sensor 113 in the optical system 1 for triglyceride inspection;

Step 4: calculate the internal turbidity Y from step 3, wherein Y is the internal turbidity caused by the triglycerides; and Step 5: show the result Y'=Y/C If C>1, then the skin tone is white or bright; therefore, Y'<Y;

If C<1, then the skin tone is dark, or the skin is rough or hairy; therefore, Y'>Y.

Figure 4:
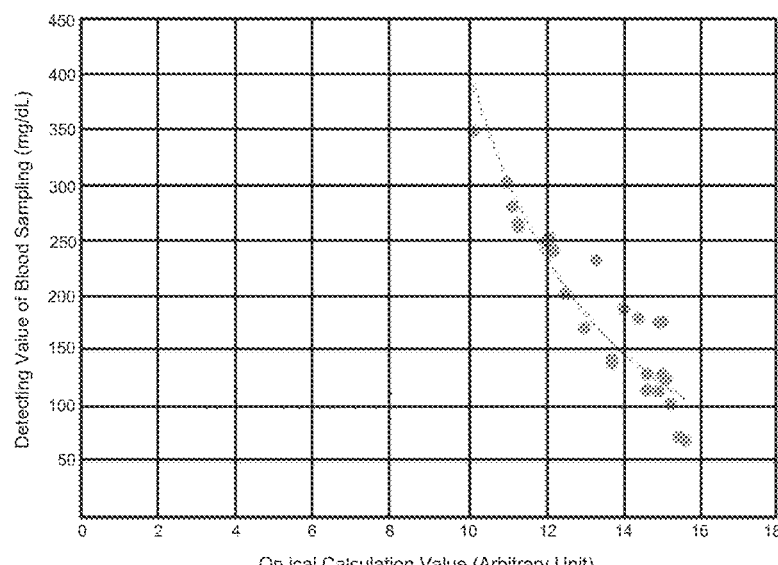
FIG. 4 is an experimental and numerical analysis diagram of the comparison between the detection results using the optical method for triglyceride inspection according to the present invention and the examining results using conventional blood sampling.

Besides, C not only represents the feature differences of the skin surface between the users, such as skin tone and hair but also represents the variation caused by the sitting position on the toilet seat. For example, C>1 means that the skin tone is brighter and whiter, and it may also represent that the skin in an inspection area onto which the emitted light is projected is tighter due to the pressure applied on the skin by the surface of the toilet seat. C<1 means that the skin tone is darker or the skin is hairier, and it may also represent that the skin in the inspection area is more relaxed. As shown in FIG. 4, the Y-axis is the detecting value originating from blood sampling (actual value), and the X-axis is the optical calculation value. The dashed line is the result of combining the two axes. The dashed line is an X-Y function, wherein Y is an optical prediction value of internal (blood) turbidity and X is a calculation value of actual optical measurement.

The relationship of X and Y in the X-Y function can be exponential, power and polynomial, etc. Through the operation of the X-Y function, the value of internal (blood) turbidity detected by the non-invasive optical system for triglyceride inspection can be obtained. In addition, said function is obtained through induction and summarization of data in the present invention.

In another feasible embodiment according to the optical system 1 for triglyceride inspection, the second light source 112 may further be a green, red or mid-infrared light.

Figure 3:
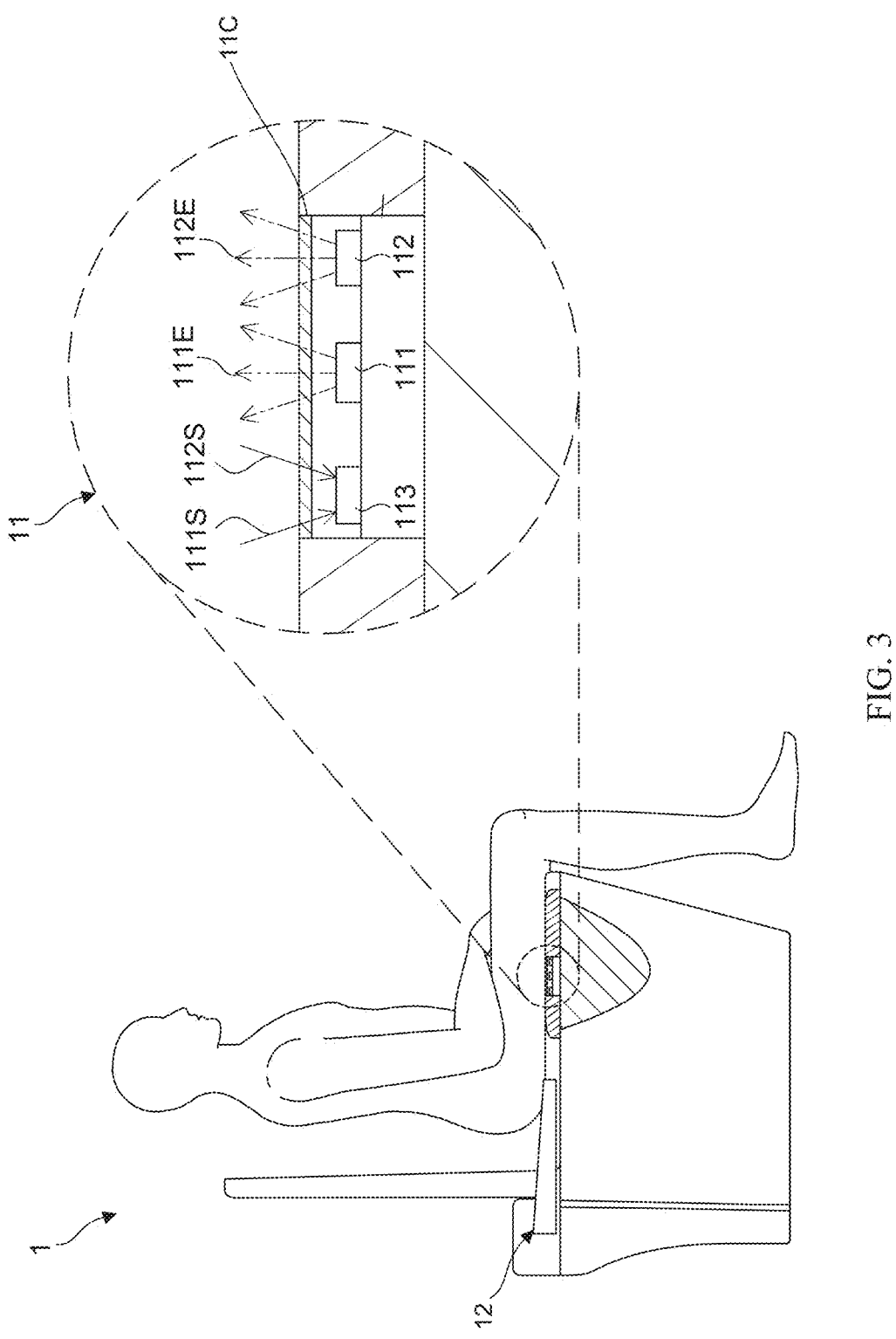
FIG. 3 is a sectional view of the optical sensor module shown in FIG. 1.

In a further feasible embodiment, as shown in FIG. 2 and FIG. 3, the optical sensor assembly 11 further comprises a transparent cover 11C, wherein the first emitted light 111E and the second emitted light 112E generated respectively by the first light source 111 and the second light source 112 are projected onto the skin of the user through the transparent cover 11C. The first scattered light 111S and the second scattered light 112S are generated respectively after the first emitted light 111E and the second emitted light 112E are projected onto the skin of the user. Then the first scattered light 111S and the second scattered light 112S are received by the optical sensor 113 through the transparent cover 11C. The first emitted light 111E and the second emitted light 112E are projected onto the skin of the user through a part of the transparent cover 11C that has a function of light divergence, such as a diverging lens. The first scattered light 111S and the second scattered light 112S are received by the optical sensor 113 through a part of the transparent cover 11C that has a function of light convergence, such as a condensing lens.

Moreover, the processor 120 is able to transmit the measured internal turbidity, through a communication interface thereof to a user-end electronic device like a smartphone, a tablet computer, a smartwatch, a smart bracelet, a door phone, a desktop computer, a laptop computer, an all-in-one computer, or a server computer.

Furthermore, another embodiment of the present invention is a toilet 2 containing an optical system 1 for triglyceride inspection as described above. As FIG. 1 shows, in such embodiment the electronic device 12 is integrated in a smart toilet control box of the toilet 2.

Second Embodiment

The basic principle of the optical system 1 for triglyceride inspection according to the present invention is that when a light source, such as the second light source 112 (LED or laser) as described in the first embodiment, emits a near-infrared (NIR) light beam of a specific wavelength (e.g. 700 to 1100 nm), the NIR light beam penetrates part of the skin depth and produces a scattered light (i.e., the second scattered light 112S in the first embodiment). Then, the scattered light is received by an optical sensor 113, and the scattered light received is used as a basis for analysis of the triglyceride concentration in the human body. In addition, since the penetration depth of different wavelengths of light to skin tissues may vary, near-infrared light (wavelength 700 to 1100 nm), which has better penetration to the skin, is selected as the main light source for the detection of triglyceride in this embodiment.

If the human body contains higher amounts of triglycerides, the optical sensor 113 will receive scattered light with higher intensity; conversely, if the human body contains fewer amounts of triglycerides, the optical sensor 113 will receive scattered light with lower intensity.

However, the skin surface characteristics of different users may vary greatly, and the variation of these skin surface characteristics, including skin tone, skin roughness, and the number of hairs, can cause the variation in the degree of absorption of the emitted light (near-infrared light) and the variation in the degree of direct scattering. Therefore, the inventors of the present application believe that it is necessary to perform an adaptive compensation (offset) of the light signal (scattered light) received by the optical sensor 113 to enhance the accuracy of inspection value of triglyceride.

In the present invention, thus a new light source, such as the first light source 111 (white LED) described in the first embodiment, is added to produce a scattered light (i.e., the first scattered light 111S in the first embodiment) on the skin surface of the user, and the first scattered light 111S is received by the optical sensor 113. Then the second light source 112 (LED or laser) as described in the first embodiment penetrates part of the skin depth with a near-infrared (NIR) light of a specific wavelength (e.g., 700 to 1100 nm) and produces a scattered light (i.e., the second scattered light 112S in the first embodiment), wherein the second scattered light is then received by the optical sensor 113. Next, the optical sensor 113 uses the received light signal (including the first scattered light 111S and the second scattered light 112S) to generate a sensing signal of an adaptive calibration function to compensate for the detection errors resulting from the differences in skin surface characteristics of different users. The adaptive calibration function is as described in the first embodiment. Later, the sensing signal is processed by the processor 120 in the electronic device 12 to determine the signal strength of triglyceride levels of the user or is converted into an inspection value of triglyceride by the processor 120. Finally, the signal strength of triglyceride levels or inspection value of triglyceride is transmitted to the display 122 for presentation to the user.

Referring to FIG. 4, it can be learned from the experimental and numerical analysis that the detection results of the optical system 1 for triglyceride inspection in the second embodiment can have the same effect corresponding to that of the conventional blood sampling. Further, through data collection and analysis, the present invention also establishes an algorithm of a non-invasive optical system for triglyceride inspection with a confidence level of 85% (R2=0.8551).

Further, as shown in Table 1 below, the optical calculation value of the optical system 1 for triglyceride inspection according to the present invention is compensated through the adaptive calibration function for detection error caused by the differences in skin surface characteristics of different users to obtain an inspection value of triglyceride. The inspection value of triglyceride corresponds to the detection value of the blood sampling, i.e., the inspection value of triglyceride is very close to the detection value obtained from blood sampling. Therefore, the results of FIG. 4 and Table 1 show that the inspection value of triglyceride obtained by the optical system 1 for triglyceride inspection according to the present invention can fully reflect the triglyceride concentration in the user's body. In other words, the inspection value of triglyceride is representative and reliable.

TABLE 1

| Optical calculation values | The detection values of the blood sampling | The value obtained by the adaptive calibration function compensating for the skin surface characteristics |
|---|---|---|
| 14.6 | 129 | 153.9839198 |
| 10.13 | 348 | 346.0126884 |
| 13.715 | 139 | 176.8594308 |
| 11.26 | 265 | 273.7533304 |
| 15.01 | 177 | 144.821724 |
| 13.29 | 232 | 189.6309032 |
| 12.16 | 242 | 230.8814695 |
| 11 | 302 | 288.2917064 |
| 11.13 | 280 | 280.8860413 |
| 12.1 | 252 | 233.4249912 |
| 13.7 | 143 | 177.2886325 |
| 12 | 248 | 237.755453 |
| 11.3 | 262 | 271.611525 |
| 12.2 | 240 | 229.208079 |
| 14.4 | 180 | 158.7610733 |
| 13.7 | 142 | 177.2886325 |
| 15.2 | 103 | 140.8423942 |
| 14.9 | 114 | 147.200526 |
| 14 | 188 | 168.9831289 |
| 14.9 | 176 | 147.200526 |
| 12.5 | 202 | 217.2007235 |
| 13 | 171 | 199.1280409 |
| 15 | 129 | 145.035664 |
| 14.6 | 115 | 153.9839198 |

In addition, in the optical system 1 for triglyceride inspection according to the present invention, the processor 120 in the electronic device 12 converts the sensing signal into an inspection value of triglyceride and transmits the inspection value of triglyceride to the display 122 for presentation to the user, and as shown in FIG. 1, the display 122 can also display the grade of triglyceride concentration according to the different inspection values of triglyceride by the following light signals:

1. green light: the normal levels, triglycerides <150 mg/dL;
2. yellow light: borderline high levels, triglycerides are between 150 to 199 mg/dL;
3. orange light: high-risk levels, triglycerides are between 200 to 499 mg/dL;

4. red light: very high-risk levels, triglycerides >500 mg/dL.

In other words, the basic principle of the above embodiment uses near-infrared light as the second light source 112 to partially penetrate the skin for detection of triglyceride concentration, but in further embodiments, practically the second light source 112 is not limited to near-infrared light and can be any light that can penetrate part of the skin depth for detection of triglycerides, such as green light (500 to 600 nm), red light (600 to 700 nm), mid-infrared light (~3 to 8 μm) and other light sources.

Third Embodiment

FIG. 5 shows a flow chart of the optical method for triglyceride inspection according to the present invention. As shown in FIG. 5 and FIG. 6, and with further reference to FIG. 3, the method includes the following steps:

S1: receiving an initiation command to start the detection of triglycerides via an input interface 123, i.e., an optical system 1 for triglyceride inspection according to the present invention receives a detection instruction from the user via the input interface 123, wherein the input interface 123 is coupled to the processor 120, and can be a physical button, a voice control module, or a touch-sensitive panel;

S2 after receiving the detection instruction, the processor 120 of the electronic device 12 sequentially activates a first light source 111 and a second light source 112 of the optical sensor assembly 11, so as to generate a first emitted light 111E and a second emitted light 112E, respectively, wherein the first light source 111 is a white light LED and the second light source 112 is a near-infrared LED (NIR LED) or a laser;

S3: receiving a first scattered light 111S and a second scattered light 112S sequentially by an optical sensor 113 of the optical sensor assembly 11, wherein the first scattered light 111S and the second scattered light 112S is generated respectively after the first emitted light 111E and the second emitted light 112E are projected onto the skin of the user's thigh;

S4: generating a sensing signal by the optical sensor 113 using the first scattered light 111S and the second scattered light 112S and transmitting the sensing signal from the optical sensor 113 to the electronic device 12, wherein the sensing signal is an adaptive calibration function according to the present invention as described above and the optical sensor 113 may be a photodiode, a CMOS sensor, a CCD sensor, or a spectrophotometer;

S5: converting the sensing signal to a signal strength of triglyceride levels or an inspection value of triglyceride by a processor 120 in the electronic device 12 to reflect the triglyceride concentration in the user's body, wherein the processor 120 may be an ARM Cortex series processor; and S6: transmitting the signal strength of triglyceride levels or the inspection value of triglyceride from the processor 120 to the display 122, wherein the display 122 is coupled to the processor 120, and may be an LED display or an LCD touch display.

In a nutshell, the above descriptions have thoroughly introduced the optical system for triglyceride inspection according to the present invention. The above descriptions are made on embodiments of the present invention; however, the embodiments are not intended to limit the scope of the present invention, and all equivalent implementations or alterations within the spirit of the present invention still fall within the scope of the present invention.

What is claimed is:

1. An optical system for triglyceride inspection, comprising:

an optical assembly (11), being integrated into a toilet seat (21), and comprising a first light source (111), a second light source (112) and an optical sensor (113); and an electronic device (12), being coupled to the optical assembly (11), and comprises a processor (120), a memory (121) and a display (122);

wherein the memory (121) is configured to store instructions, and the processor (120) is configured to execute the instructions to:

radiate, by enabling the first light source (111), a white light onto a skin of a subject, thereby causing a first scattered light to be produced from the skin;

collect, by enabling the optical sensor (113), the first scattered light;

calculate, based on the first scattered light and the white light, an estimated reflectance;

calculate, by utilizing a first mathematical expression: C=Counts white light/Counts baseline, a calibration coefficient; wherein Counts white light is the estimated reflectance, and Counts_baseline represents a reference reflectance;

radiate, by enabling the second light source (112), a detection light onto the skin of the subject, thereby causing a second scattered light to be produced from the skin;

collect, by enabling the optical sensor (113), the second scattered light;

calculate, based on the second scattered light and the detection light, an estimated internal turbidity;

calculate, by utilizing a second mathematical expression: Y'=Y/C, a measured internal turbidity; wherein Y is the estimated internal turbidity, and C is the calibration coefficient; and show, by driving the display (122), the measured internal turbidity.

2. The optical system for triglyceride inspection of claim 1, wherein the detection light is a near-infrared light.

3. The optical system for triglyceride inspection of claim 2, wherein when the skin is white or bright, the calibration coefficient is greater than 1, thereby leading the measured internal turbidity to be less than the estimated internal turbidity.

4. The optical system for triglyceride inspection of claim 3, wherein when the skin is dark, the calibration coefficient is less than 1, thereby leading the measured internal turbidity to be greater than the estimated internal turbidity.

5. The optical system for triglyceride inspection of claim 4, wherein the detection light has a wavelength in a range between 700 and 2500 nm.

6. The optical system for triglyceride inspection of claim 4, wherein the detection light has a wavelength in a range between 700 and 1100 nm.

7. The optical system for triglyceride inspection of claim 1, wherein the detection light is a green light, a red light, or a mid-infrared light.

8. The optical system for triglyceride inspection of claim 1, wherein the processor (120) is further configured to transmit the measured internal turbidity to a user-end electronic device that is selected from a group consisting of smartphone, tablet computer, smartwatch, smart bracelet, door phone, desktop computer, laptop computer, all-in-one computer, and server computer, and wherein the electronic device is configured to be integrated in a smart toilet control box.

9. A toilet comprising the optical system for triglyceride inspection of claim 1.

* * * * *